(12) United States Patent
Thakur et al.

(10) Patent No.: US 9,788,742 B2
(45) Date of Patent: Oct. 17, 2017

(54) IMPEDANCE WAVEFORM MONITORING FOR HEART BEAT CONFIRMATION

(71) Applicant: CAMERON HEALTH, INC., St. Paul, MN (US)

(72) Inventors: Pramodsingh Hirasingh Thakur, Woodbury, MN (US); Viktoria A. Averina, Roseville, MN (US); Amy J. Brisben, St. Paul, MN (US); Krzysztof Z. Siejko, Maple Grove, MN (US)

(73) Assignee: Cameron Health, Inc., St. Paul, MN (US)

( * ) Notice: Subject to any disclaimer, the term of this patent is extended or adjusted under 35 U.S.C. 154(b) by 197 days.

(21) Appl. No.: 14/609,059

(22) Filed: Jan. 29, 2015

(65) Prior Publication Data

US 2015/0216433 A1  Aug. 6, 2015

Related U.S. Application Data

(60) Provisional application No. 61/935,371, filed on Feb. 4, 2014.

(51) Int. Cl.
| | |
|---|---|
| *A61B 5/04* | (2006.01) |
| *A61N 1/37* | (2006.01) |
| *A61B 5/00* | (2006.01) |
| *A61N 1/365* | (2006.01) |
| *A61B 5/053* | (2006.01) |
| *A61B 5/0452* | (2006.01) |

(52) U.S. Cl.
CPC .......... *A61B 5/04012* (2013.01); *A61B 5/053* (2013.01); *A61B 5/686* (2013.01); *A61N 1/36521* (2013.01); *A61N 1/3706* (2013.01); *A61B 5/0452* (2013.01)

(58) Field of Classification Search
CPC . A61B 5/04012; A61B 5/0452; A61B 5/0402; A61B 5/053; A61B 5/686; A61N 1/36521; A61N 1/3706; A61N 1/37
See application file for complete search history.

(56) References Cited

U.S. PATENT DOCUMENTS

| | | |
|---|---|---|
| 5,709,215 A | 1/1998 | Perttu et al. |
| 6,647,292 B1 | 11/2003 | Bardy et al. |
| 6,721,597 B1 | 4/2004 | Bardy et al. |
| 6,754,528 B2 | 6/2004 | Bardy et al. |
| 7,149,575 B2 | 12/2006 | Ostroff et al. |
| 7,248,921 B2 | 7/2007 | Palreddy et al. |
| 7,330,757 B2 | 2/2008 | Ostroff et al. |
| 7,376,458 B2 | 5/2008 | Palreddy et al. |
| 7,392,085 B2 | 6/2008 | Warren et al. |
| 7,477,935 B2 | 1/2009 | Palreddy et al. |
| 7,623,909 B2 | 11/2009 | Sanghera et al. |
| 7,623,913 B2 | 11/2009 | Phillips |
| 7,813,791 B1 | 10/2010 | Gill et al. |
| 8,116,867 B2 | 2/2012 | Ostroff |

(Continued)

*Primary Examiner* — Mallika D Fairchild
(74) *Attorney, Agent, or Firm* — Seager, Tufte & Wickhem LLP

(57) ABSTRACT

Implantable systems and methods directed toward improved accuracy in cardiac signal analysis. An impedance waveform is captured and used to confirm the analysis performed by the system on electrical signals or electrocardiogram. A detected heart beat from the electrocardiogram is either confirmed or identified as a misdetection depending on whether the impedance waveform shows likely correct or incorrect detection. Identified misdetection can then be corrected or otherwise mitigated.

18 Claims, 12 Drawing Sheets

(56) References Cited

U.S. PATENT DOCUMENTS

| | | |
|---|---|---|
| 8,160,686 B2 | 4/2012 | Allavatam et al. |
| 8,160,687 B2 | 4/2012 | Warren et al. |
| 8,160,697 B2 | 4/2012 | Warren et al. |
| 8,200,341 B2 | 6/2012 | Sanghera et al. |
| 8,260,404 B1 | 9/2012 | Bharmi et al. |
| 8,265,737 B2 | 9/2012 | Warren et al. |
| 8,483,841 B2 | 7/2013 | Sanghera et al. |
| 8,494,630 B2 | 7/2013 | Palreddy et al. |
| 8,565,878 B2 | 10/2013 | Allavatam et al. |
| 2009/0228057 A1 | 9/2009 | Allavatam et al. |
| 2011/0098775 A1 | 4/2011 | Allavatam et al. |

IMPEDANCE WAVEFORM MONITORING FOR HEART BEAT CONFIRMATION

RELATED PATENT DOCUMENTS

This application claims the benefit of and priority to U.S. Provisional Patent Application Ser. No. 61/935,371, filed on Feb. 4, 2014 and titled IMPEDANCE WAVEFORM MONITORING FOR HEART BEAT CONFIRMATION, the entire disclosure of which is incorporated herein by reference.

BACKGROUND

Implantable cardiac devices typically sense cardiac electrical signals in an implantee and classify the implantee's cardiac rhythm as normal/benign or treatable/malignant. Illustrative malignant rhythms may include ventricular fibrillation and/or polymorphic ventricular tachyarrhythmia. Other rhythms may also be considered malignant or treatable, such as bradycardia or monomorphic tachyarrhythmia. The accuracy with which an implantable medical device analyzes sensed signals determines how well it makes therapy determinations and other decisions.

New and/or alternative methods and devices for cardiac signal analysis are desired.

SUMMARY

Various illustrative embodiments of the present invention are directed toward improved accuracy in cardiac signal analysis by implantable medical devices. Some illustrative embodiments identify overdetection of events. Some illustrative embodiments also correct at least some detection data and use the corrected data to make operational decisions. The invention may be embodied in methods, devices and/or systems.

In an illustrative example, an implantable device detects events, which are intended to represent heart "beats", using electrocardiogram (ECG) data and, when needed, confirms the detected events using analysis of an impedance waveform. In one example, the device injects current and monitors a resultant voltage at a sampling rate in order to generate an impedance waveform. Characteristics of the impedance waveform are then analyzed to determine whether misdetection of the cardiac rhythm has occurred.

Illustrative examples analyze one or more of the integral of the impedance waveform, the alignment of peaks of the impedance waveform to ECG peaks, or the derivative, slope, polarity and/or magnitude for the impedance waveform in a predetermined time frame. Other examples may reference other characteristics of the impedance waveform, and may include generation of an impedance waveform template, for example. Details of these illustrative examples, and others, are provided below.

If analysis of the impedance waveform concludes that misdetection is occurring, then corrective action is taken by the system. Corrective action may include modifying an ECG sensing operation, changing ECG sensing vectors, triggering a patient alert, correcting stored data relating to misdetected signals, delaying or withholding therapy, or storing and flagging data for later assessment of sensing characteristics. If analysis of the impedance waveform confirms correct detection of the ECG, then device operation may go forward unchanged.

In an alternative embodiment, characteristics of the impedance waveform are used to trigger R-wave detection. For example, identified features of the impedance waveform can be used to set a window for R-wave detection in the ECG signal.

This summary is intended to provide an overview of subject matter of the present patent application. It is not intended to provide an exclusive or exhaustive explanation of the invention. The detailed description is included to provide further information about the present patent application.

DETAILED DESCRIPTION

Figure 1:
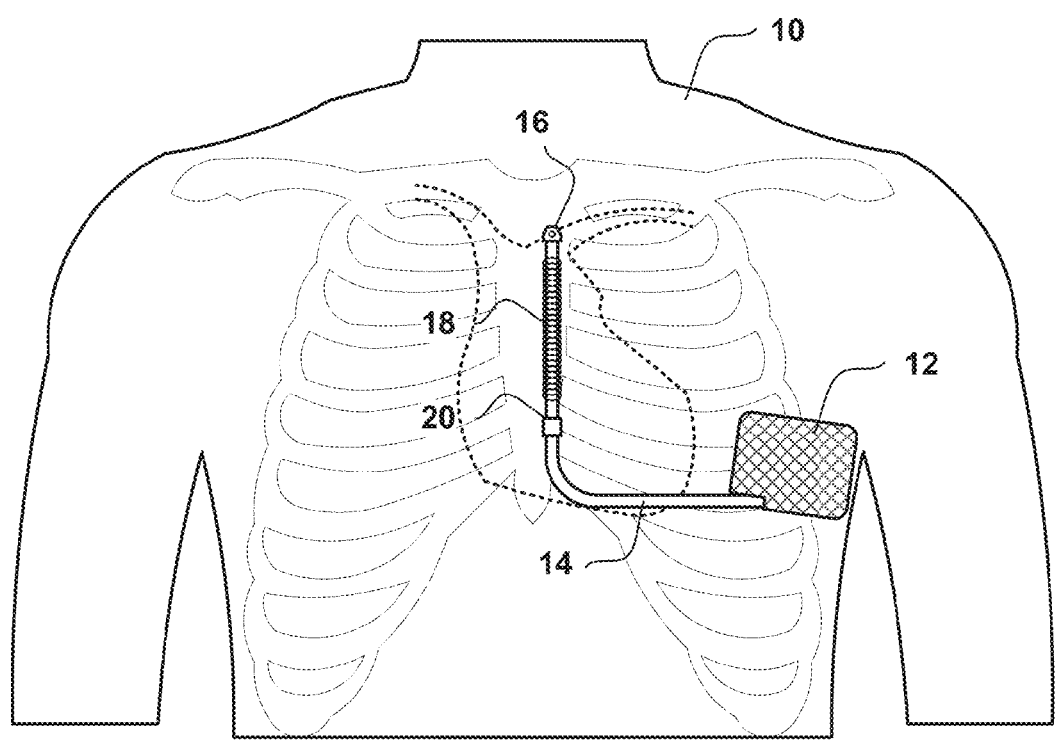
FIG. 1 shows an illustrative implant of a subcutaneous-only cardiac system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

As used herein, the term "beat" or phrases "cardiac beats" or "heart beats" are all intended to refer to a cardiac cycle. The typical cardiac cycle includes a number of individual components, including P, Q, R, S and T waves. For implantable cardiac therapy or monitoring systems, counting of cardiac beats or cycles is often the starting point of analysis. Achieving high accuracy, with both high sensitivity and specificity to beats is desirable.

Implantable systems typically seek to detect events in the electrical cardiac signal, the ECG, with the events being indicative of cardiac cycles or beats. A common approach is to design a system to detect the depolarization of the ventricles (the R-wave or QRS complex). In some systems with atrial leads and/or sensing capability, depolarization of the atria (the P-wave) can be used to detect cardiac cycles or beats.

FIG. 1 shows an illustrative implant position of a subcutaneous-only cardiac system. Historically, early implantable defibrillators initially included patch electrodes placed on the heart itself, known as epicardial electrodes. Epicardial electrodes would typically be placed by thoracotomy, an invasive procedure carrying risks of infection, and the epicardial patch electrodes used were prone to failure.

The transvenous defibrillator lead was introduced to avoid the significant risks and intrusion of the thoracotomy and epicardial electrodes and leads, while still allowing the electrodes to be placed inside the heart. Although failure rates dropped relative to the epicardial system, transvenous leads can fail, and may also provide an avenue for an infection to access the bloodstream.

A subcutaneous-only system was later introduced in order to overcome some of the difficulties of both transvenous and epicardial systems. Illustrative subcutaneous-only systems are shown in U.S. Pat. Nos. 6,647,292, 6,721,597, and 7,149,575, each of which is incorporated herein by reference. Some illustrative configurations for the lead 14 are discussed in U.S. Pat. No. 8,483,841, which is also incorporated herein by reference.

The implant shown in FIG. 1 generally corresponds to that of the S-ICD® System, approved by the US Food and Drug Administration in 2012. The implantable system is implanted outside of the ribcage of the patient 10, and includes a canister 12 coupled to a lead 14. The lead 14 includes electrodes 16, 18 and 20. When implanted according to the original S-ICD® System instructions, the canister 12 is in the left axilla, while the lead 14 extends to the left side of the sternum with the coil electrode 18 more or less parallel to the sternum. The canister 12 may be implanted such that the lead 14 runs along or below the inframammary crease. Other implant locations have been proposed and tested, and that shown in FIG. 1 is merely illustrative of one example.

Sensing presents new challenges for a subcutaneous-only system because, unlike predecessor transvenous or epicardial systems, no sensing electrodes are placed in or on the heart of the patient 10. This causes the sensed signal to have a lower signal-to-noise ratio and amplitude than earlier systems. The signals, such as the R-wave and T-wave, are also wider than that encountered by near field sensing configurations of transvenous systems. As a result, T-wave overdetection, noise and other oversensing sources must be addressed.

Examples of methods for detecting signals, eliminating overdetection and discriminating arrhythmias are shown, for example, in US Pub. Pat. App. No. 2009-0228057, U.S. Pat. No. 6,754,528, U.S. Pat. No. 7,248,921, U.S. Pat. No. 7,330,757, U.S. Pat. No. 7,376,458, U.S. Pat. No. 7,392,085, U.S. Pat. No. 7,477,935, U.S. Pat. No. 7,623,909, U.S. Pat. No. 7,623,913, U.S. Pat. No. 8,116,867, U.S. Pat. No. 8,160,697, U.S. Pat. No. 8,160,686, U.S. Pat. No. 8,160,687, U.S. Pat. No. 8,200,341, U.S. Pat. No. 8,265,737, and U.S. Pat. No. 8,494,630, each of which is incorporated herein by reference. The present inventors have recognized that further enhancements are available by capturing and using an impedance waveform.

For example, U.S. Pat. No. 7,623,909 describes ECG sensing configuration for an implantable device. In the U.S. Pat. No. 7,623,909, in an illustrative example, a first sensing vector is analyzed to determine whether it is suitable, within given threshold conditions, for use in cardiac event detection and analysis. If so, the first vector may be selected for detection and analysis. Otherwise, one or more additional vectors are analyzed. A detailed example illustrates methods for analyzing sensing vectors by the use of a scoring system. Devices adapted to perform these methods are also discussed in U.S. Pat. No. 7,623,909, including implantable medical devices adapted to perform these methods, and systems comprising implantable medical devices and programmers adapted to communicate with implantable medical devices, the systems also being adapted to perform these methods.

Figure 2:
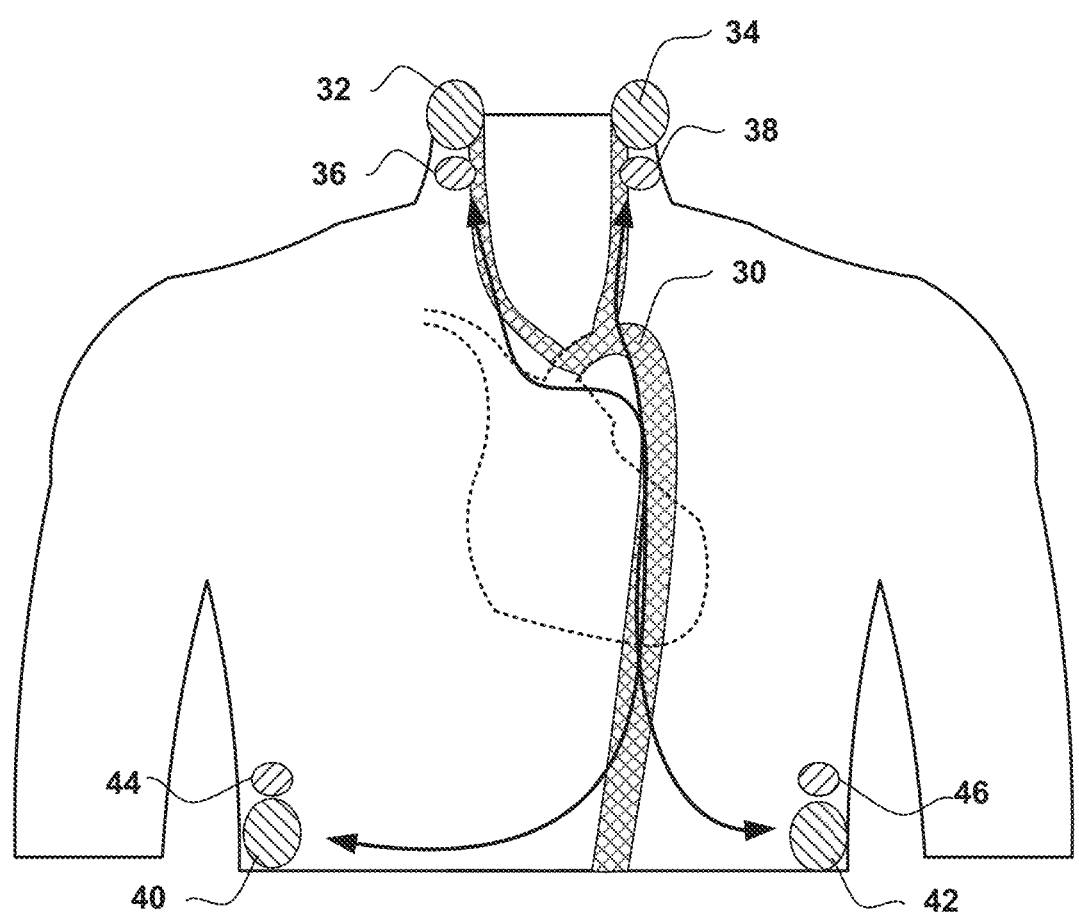
FIG. 2 illustrates a system for impedance cardiography.

FIG. 2 illustrates a system for impedance cardiography. A set of surface electrodes are used in this example. Four pairs of electrodes are placed on the skin of the patient, with pairs on the right side of the neck at 32/36, the left side of the neck at 34/38, near the first and second ribs on the left side 40/44 of the ribcage, and again near the first and second ribs on the right side 42/46 of the ribcage.

In the system of FIG. 2, current is injected using the outer electrodes 32/34 and/or 40/42, and a measure of pulsatile flow through the aorta 30 is determined by observing fluctuations in the impedance using inner electrodes 36/38 and 44/46. The placement of electrodes as shown allows the bulk of the injected current to pass through the aorta 30. The inventors have recognized that the placement of electrodes in a system as shown in FIG. 1 would also be suitable to inject low level current (preferably below the activation threshold for skeletal muscle) flow through the aorta and enable impedance cardiography.

Figure 3:
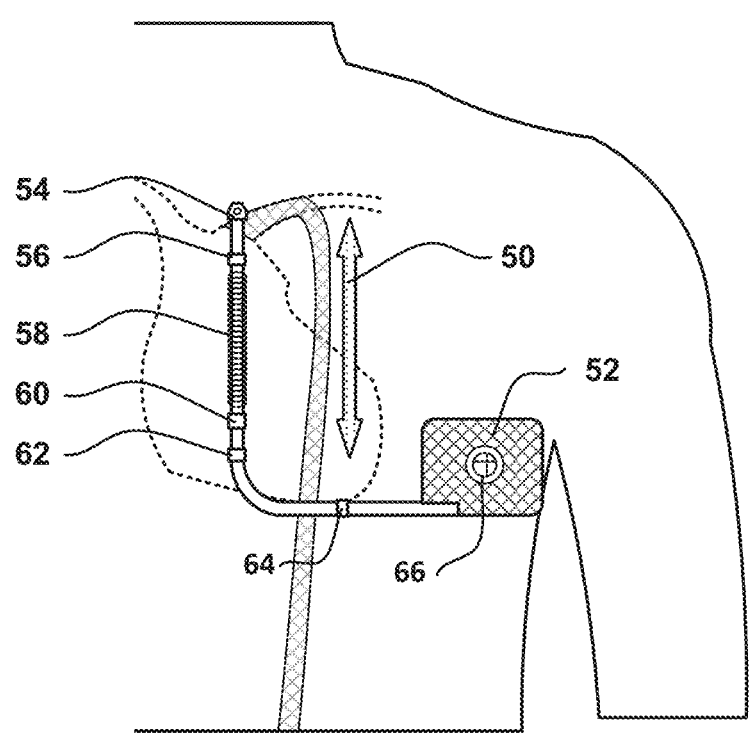
FIG. 3 shows an illustrative implantable subcutaneous cardiac system with enhancements for impedance cardiography.

FIG. 3 shows an illustrative implantable subcutaneous cardiac system with enhancements for impedance cardiography. The goal in the impedance cardiography is to inject current that will run through the aorta, along arrow 50. The illustrative system in FIG. 3 includes several "extra" electrodes, one or more of which may be included for impedance waveform monitoring. Not all of the electrodes would be needed in any particular embodiment.

The electrodes include a canister electrode 52 that makes up much of the surface of the canister, a distal tip electrode 54, shown with an optional suture hole, a coil electrode 58, and a near-xiphoid electrode 62, much as shown above in FIG. 1. FIG. 3 also shows electrode 56 between electrodes 54 and 58, as well as electrode 60 between electrodes 58 and 62, and proximal lead electrode 64 disposed proximal of the xiphoid electrode 62. The canister is shown as also including a button electrode 66 which is isolated from the rest of the conductive surface electrode 52.

In use, electrodes 56 and 58 may be coupled to the coil electrode 58 during high power therapy delivery (such as defibrillation) but otherwise isolated from the coil 58. The button electrode 66 may be coupled to the conductive surface 52 during high power therapy but otherwise isolated as well. Alternatively, each electrode could be independent of each other electrode at any time.

Several different ways to inject and monitor current are provided in the system of FIG. 3. For example, current could be injected and monitored using any of these following pairings:

| Injection | Monitor |
| --- | --- |
| 52/54 | 66/56 |
| 66/54 or 52/54 | 64/56 |
| 64/54 | 62/56 |
| 62/54 | 60/56 |

Other pairings could be used, as desired, and not all of the electrodes shown 52, 54, 56, 58, 60, 62, 64, and 66, would be needed in any given system. Current could also be injected using more than 2 electrodes in order to enable steering of the current field to better align the field with the descending aorta.

For a surface system as shown in FIG. 2, the injected current may be in the range of 4 mA, applied at a frequency of 100 kHz. The applied frequency may be higher or lower, for example in the range of 1 kHz up to 1 MHz. Lower currents may be needed in an implantable system since the tissue interface at the skin is avoided. Thus injected currents may range from about 1 µA up to about 4 mA, though lower and higher boundaries conditions may be set if desired. As noted, three or more electrodes may be used simultaneously if desired, with different currents through different pairs. Various sampling rates may be used as well, down to 128 Hz, for example, with 256 up to 1024 Hz suggested. Current would not need to be continuously injected; instead, a few cycles of current input would be applied while a sample is taken, and then current flow would stop until the next sample occurs.

In one example, to save power, the impedance cardiography data gathering process may be triggered by an ECG beat detection, and takes place during only a limited time period following beat detection. In one example, impedance cardiography is performed by injecting current and taking 25 samples at 256 Hz sampling rate, using a 100 kHz injection frequency and with each sample associated with a handful of cycles of current injection at 50 µA. The 256 Hz sampling rate for 25 samples gives a 100 millisecond (ms) interval during which the impedance cardiography signal is captured at high rate.

In another example, the signal sampling for impedance cardiography has high and low settings, rather than on-off as just described. In this example, impedance cardiography may be performed at a slow rate (32 Hz, for example) except during a predefined period after a beat is detected, when high rate sampling (1 kHz, for example) is performed. Other numerical solutions may apply. For certain examples that refer to an integral of the impedance waveform between two beats (see FIG. 6, below), rather than on/off or high/low settings, the device may look for certain triggers for performing the impedance cardiography function at all. For example, impedance cardiography may be performed if the calculated cardiac rate is in a predefined range, rather than performing it all the time.

Figure 4:
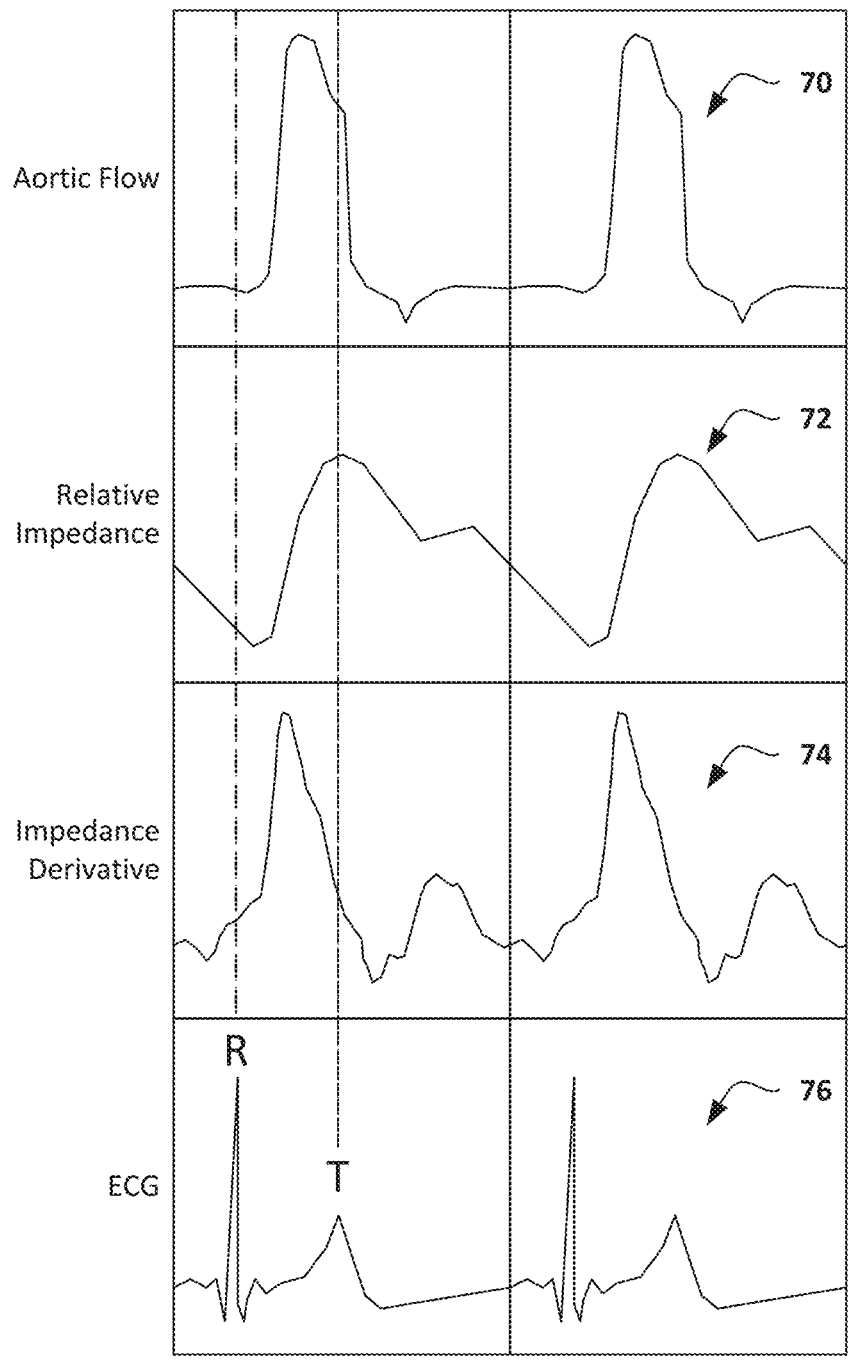
FIG. 4 shows a time-synchronized comparison of aortic flow, relative impedance and derivative, and the ECG, during cardiac cycles.

FIG. 4 shows a time-synchronized comparison of aortic flow 70, relative impedance 72, derivative of the relative impedance 74, and the ECG 76, during cardiac cycles. Vertical lines are provided to correspond to the R-wave and T-wave from the ECG 76.

As can be seen, at the end of the electrical signal for the ventricular depolarization (R-wave or QRS complex), aortic flow 70 reaches a maximum. The relative impedance 72 moves upward in correlation to the increased aortic flow, a phenomenon highlighted by the impedance derivative 74. Aortic flow drops quickly, and even reverses slightly, at the end of the ventricular contraction, which corresponds to the repolarization (T-wave) of the ventricles. As used herein, the relative impedance sampled over time is referred to as the "impedance waveform."

To the implantable device system, the R-wave and T-wave are electrically distinguishable in many cases by differences in amplitude and width or frequency content. However, these differences do not always appear readily to the implantable system. As the Inventors have recognized, reference to the impedance (and its changes), which is representative of the physical manifestation that results from the R-wave and T-wave, may be useful to improve or confirm detection accuracy.

Figure 5:
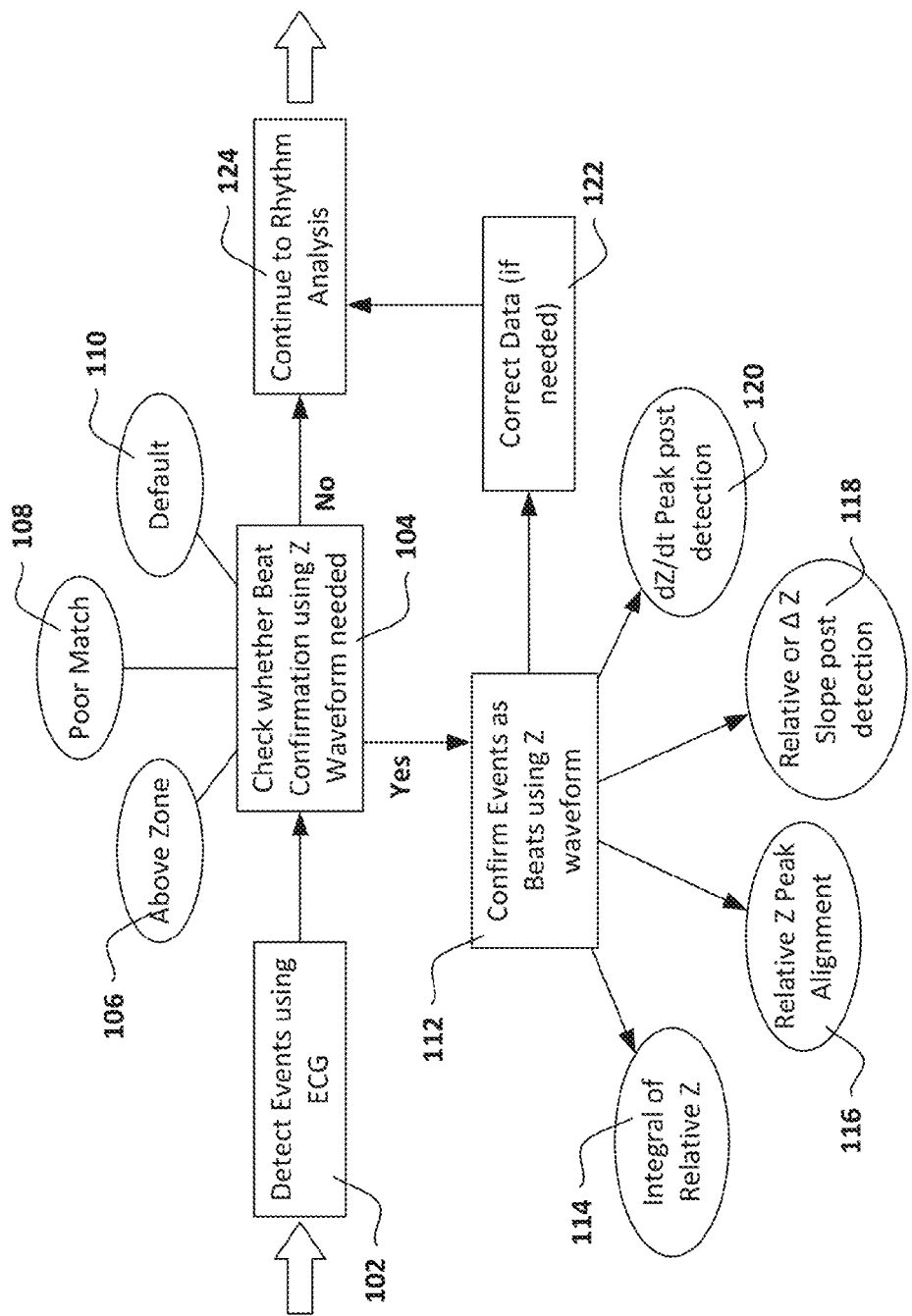
FIG. 5 illustrates a number of methods and reasons for confirming ECG beat detection using impedance analysis.

FIG. 5 illustrates a number of methods and reasons for confirming ECG event detection using impedance analysis. Overall, a method for beat confirmation begins with detecting events using the electrical signal, as shown at 102. Illustrative methods are shown in U.S. Pat. No. 8,565,878, titled ACCURATE CARDIAC EVENT DETECTION IN AN IMPLANTABLE CARDIAC STIMUS DEVICE, the disclosure of which is incorporated herein by reference. Other R-wave detectors may be used instead.

Next, as an optional step, the method determines whether beat confirmation using the impedance (Z in FIG. 5) waveform is needed, as shown at block 104. Example bases for determining that confirmation is needed may include checking whether the detected rate is above a preset zone, as shown at 106. Another criteria, shown at 108, may include determining that a particular beat is a poor match to a template, where the template may be a morphology template, a frequency domain template, a wavelet transform template, a width and/or amplitude, or other indicator of anticipated beat features. As a third "criteria", the system may simply include a default setting to confirm beats using the impedance waveform, as shown at 110.

When the answer at 104 is "Yes", the system continues to block 112 to confirm one or more beats. Various metrics can be used. One example, noted at 114, uses an integral of the relative impedance, discussed below with reference to FIG. 6. Another example, noted at 116, determines peak alignment between the impedance waveform and the detected peaks, which can distinguish an R-wave from a T-wave as further discussed below relative to FIG. 7. A further example, noted at 118, assesses the slope of the impedance waveform following the ECG detection, as explained below in reference to FIG. 8. Yet another example is shown at 120, which looks at the derivative of the impedance waveform, as discussed in reference to FIG. 9, below.

Depending on whether event detection is confirmed or not, data can then be corrected as shown at 122. Methods for response to identification of overdetection are shown in U.S. Pat. Nos. 8,160,686 and 8,160,687, each entitled METHODS AND DEVICES FOR ACCURATELY CLASSIFYING CARDIAC ACTIVITY, the disclosure of which is incorporated herein by reference. For example, if there are three consecutive detected events, and the middle event is identified as an overdetection, then the middle event can be discarded and an interval from the first event to the third event can be calculated and used to determine an average inter-event interval, which can in turn be used to calculate a beat rate for purposes of rhythm discrimination. To use a combined interval between such first and third events, a system may require that each of the first and third events pass the confirmation step at 112. Otherwise, in some examples, the system may instead conclude that a detected event is suspect, and at least one detection as well as adjacent intervals are unusable for rate calculation, as discussed in the '686 and '687 patents.

Other approaches to data correction 122 may be used instead. In another example, rather than or in addition to data correction, ameliorative steps may be taken such as changing a sensing vector, changing a sensing setting, suspending therapy delivery, enabling additional data analysis, setting a flag for inappropriate sensing, or applying a new or different filtering scheme.

Following data correction 122, the method continues to perform rhythm analysis, as noted at 124. Rhythm analysis typically includes some consideration of rate, and may also include analysis of beat morphology. Some examples are discussed in U.S. Pat. Nos. 8,160,686 and 8,160,687, for example.

Figure 6:
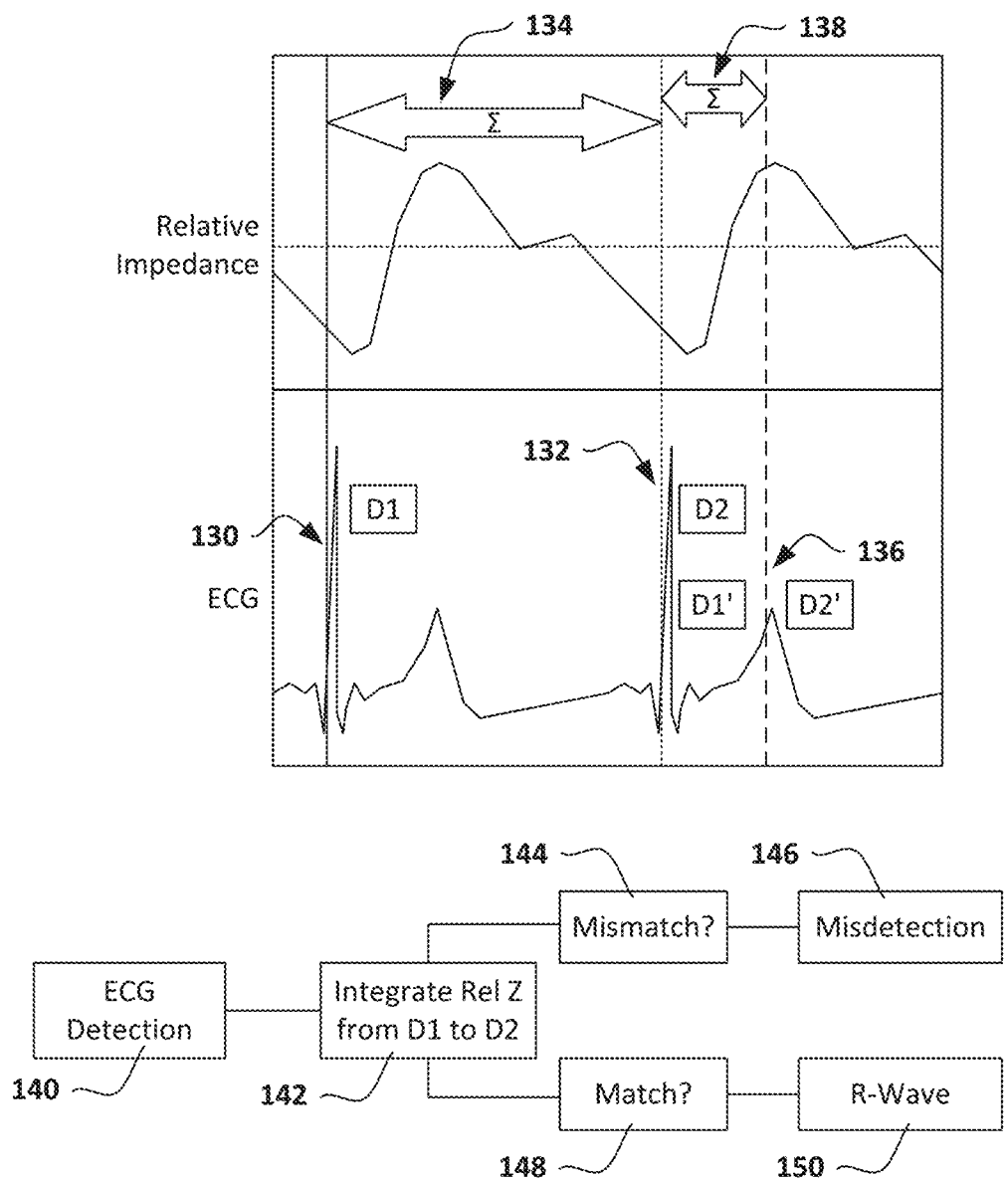
FIGS. 6-9 illustrate methods for confirming ECG beat detection using an impedance waveform.

FIG. 6 shows the use of an integral of the impedance waveform for beat confirmation. Two detected beats using R-waves are noted in the ECG, at 130 and 132. The purpose of this embodiment is to integrate the impedance waveform across an interval defined by the two detected events, as shown at 134. Where two R-waves are detected, the integral of the impedance waveform will be zero, if sensed perfectly, or at least close to zero, between the two R-waves, once baseline is removed. On the other hand, between an R-wave and T-wave, the integral of the impedance waveform will be non-zero after accounting for the baseline. Thus in the example shown an integral across interval 138, from the detected R-wave at 132 to the detected T-wave at 136, will yield a non-zero result, relative to baseline. The non-zero result allows the overdetection of the T-wave to be identified.

The method is also shown in block form and begins with an ECG detection, as shown at 140. Next, the impedance waveform is integrated across the interval between two detections, D1 and D2, as shown at 142. In some examples, the method is used to confirm a first detection by looking at the interval to a subsequent detection; in other examples, the method is used to confirm a second detection by looking at the interval from a preceding detection. Either way, the integrated quantity is then compared to a value representative of the expected integral result. If the integrated quantity is a mismatch from the expected value, as shown at 144, the method concludes that a misdetection has occurred, as shown at 146. On the other hand, if the integrated quantity is a match to the expected value (within a reasonable band such as +/−10%), as shown at 148, the method concludes that an R-wave has likely been detected, as shown at 150.

To perform the comparison at 142, one first calculates the longer-term baseline impedance for the system. This can be done using a set value or, more preferably, a review of the average of the last "N" measurements of impedance, where "N" is a large number to allow an average over several cardiac cycles to be calculated. Then, one would calculate the sum of the baseline times the duration from D1 to D2, and compare to the actual integral. In this way, the integrated impedance values are corrected to account for interval size by subtracting out the baseline impedance. In another example, the integral at 142 may be applied to the derivative of the impedance, which will remove the constant baseline from the analysis. In another example, a filter may be applied to remove the DC component of the relative impedance.

The term misdetection is used at block 146. In some examples, a misdetection is automatically deemed an overdetection correctable by dropping it and combining the intervals before and after the misdetected event. In other examples, a misdetection is presumed to be a suspect event requiring both the event and intervals before and after it to be discarded, unless both the immediately preceding and immediately following detected events are proved reliable by, for example, confirming each using methods shown herein or other methods such as template analysis.

Figure 7:
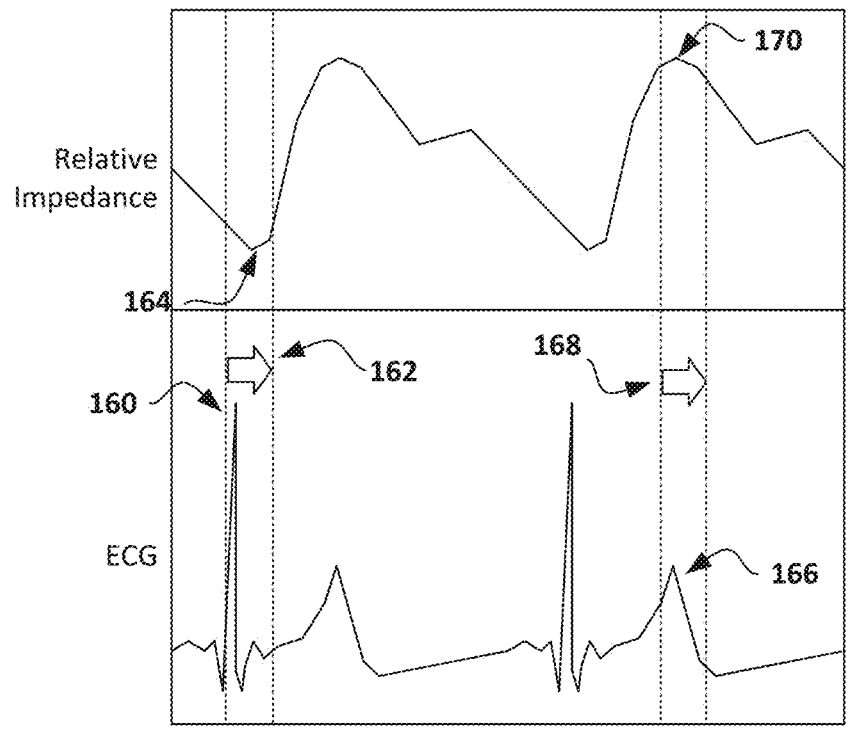
Figure 7:
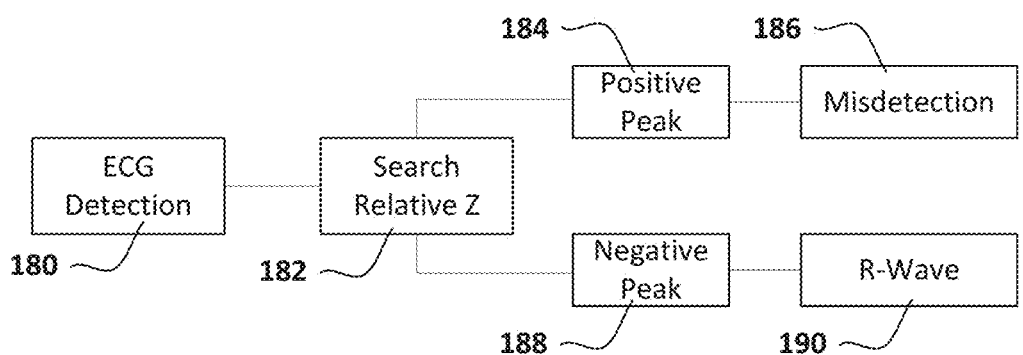

FIG. 7 shows the assessment of peak alignment between ECG and the impedance waveform for beat confirmation. An R-wave is shown at 160. Following the R-wave, a search period is defined, as shown at 162, during which a negative peak in the relative impedance is sought, as shown at 164. If such a negative peak 164 is found, then the system concludes that the detected event is likely an R-wave. If no negative peak is found, however, the system will conclude that a misdetection has occurred.

In FIG. 7, analysis of a misdetection is illustrated when the T-wave at 166 is detected. During the corresponding search period 168, a positive peak of the relative impedance is found, as shown at 170. As a result, here, the system will determine that a detected event corresponding to the T-wave 166 is a likely misdetection.

The method is displayed in block form as well. Beginning with an ECG detection 180, the method searches the waveform of the relative impedance, as shown at 182. If a positive peak is found, as shown at 184, then a misdetection is declared, as shown at 186. On the other hand, if a negative peak is found, at shown at 188, then an R-wave is declared, as shown at 190.

The criteria in FIG. 7 may be modified from that shown. For example, a positive peak may be sought at 184, while block 188 merely seeks "not peak" in the impedance waveform. Conversely, the negative peak may be sought at 188, and "no negative peak" sought at 184.

Figure 8:
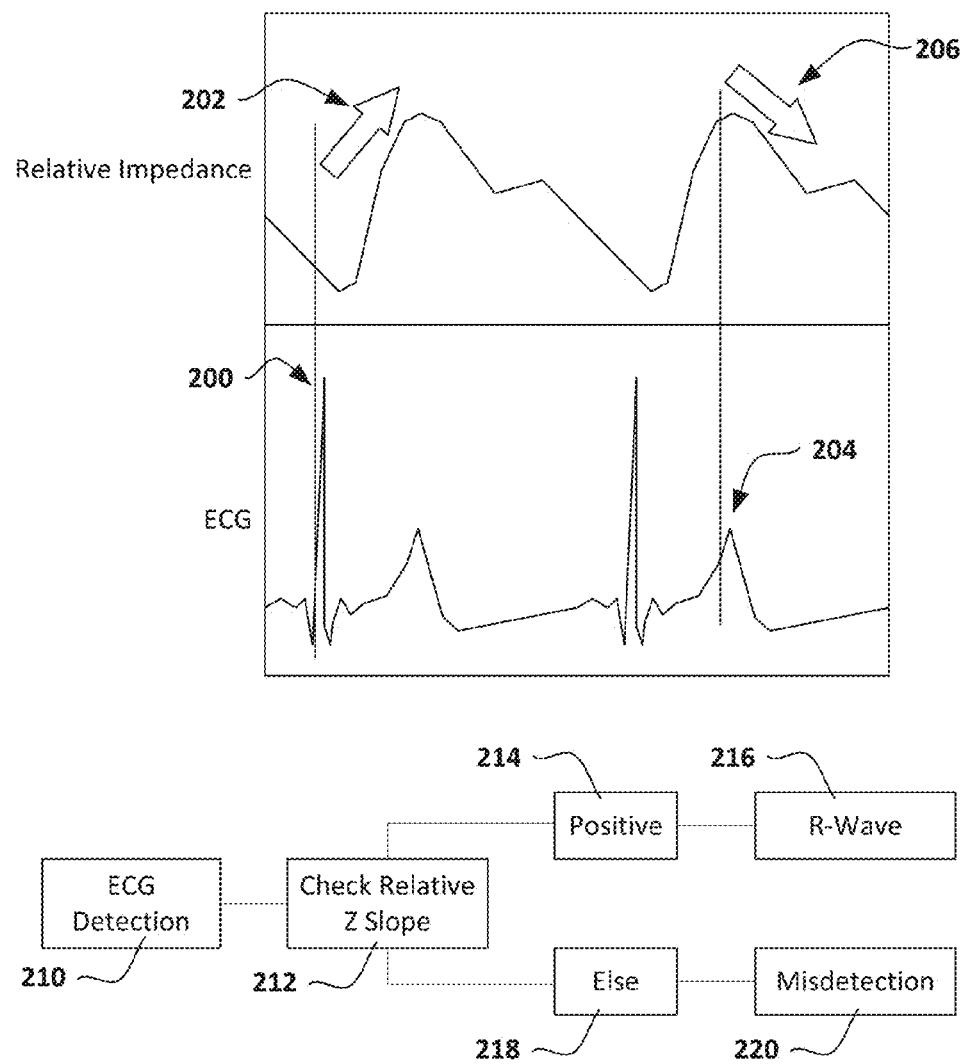

FIG. 8 shows analysis of the impedance waveform slope following an ECG-based detection for beat confirmation. In the graphic, a first detected event occurs at 200, corresponding to the R-wave in the ECG. The relative impedance slope is then analyzed.

Following an R-wave or QRS complex detection 200, the relative impedance slope is positive, as shown at 202.

A subsequent detection is shown relative to a T-wave in the ECG, at 204. Now, following the T-wave, the slope of the impedance waveform is negative, as shown at 206. As a result, a positive slope can be correlated to the R-wave, while a negative slope is correlated to the T-wave.

The method is displayed again in block form. Following ECG detection at 210, the method next checks the slope of the impedance waveform, as shown at 212. If the slope is positive, as shown at 214, the method concludes that the detected event is an R-wave, as noted at 216. If the slope is not positive, as shown at 218, then a misdetection is declared as shown at 220.

Figure 9:
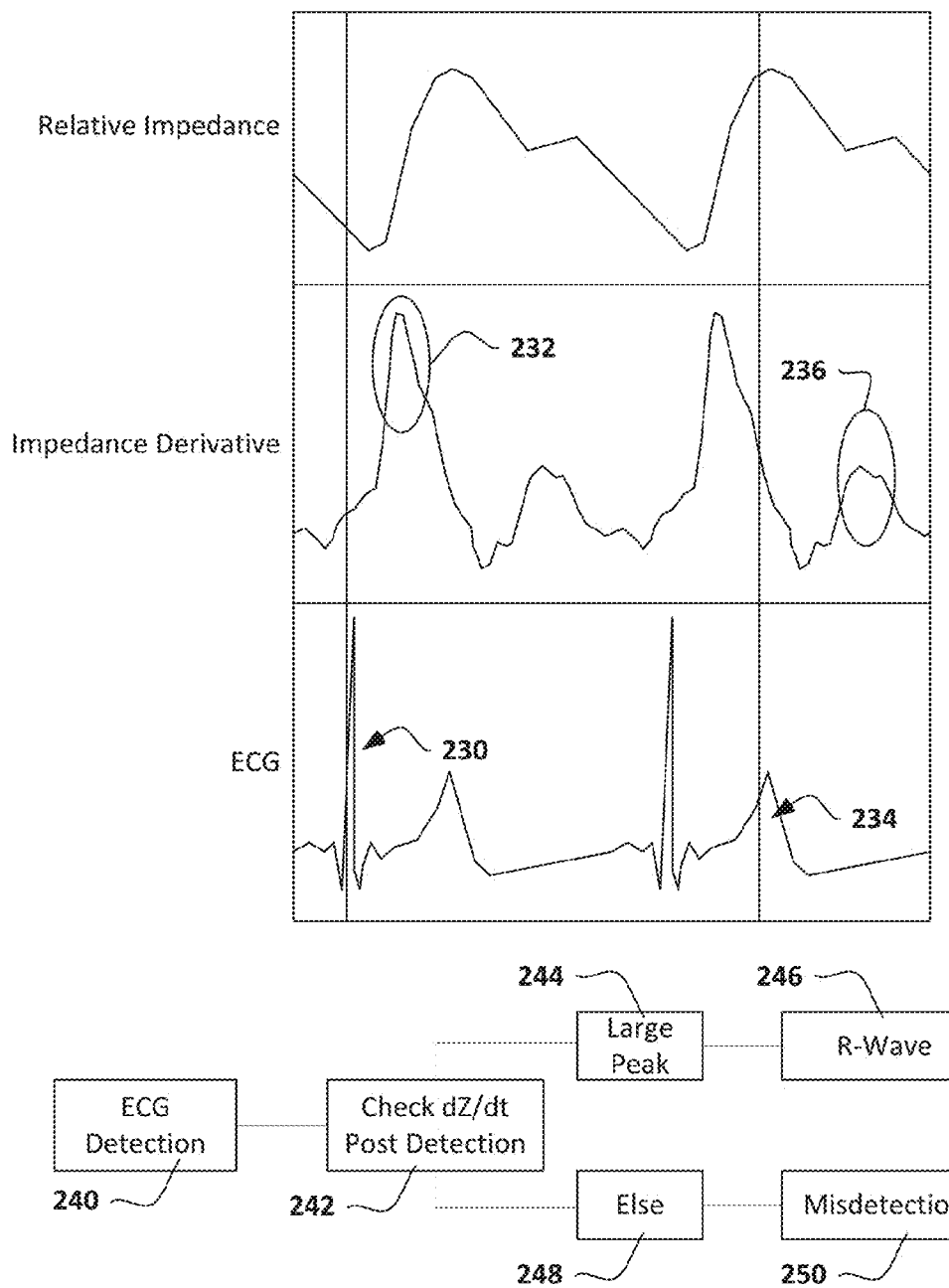

FIG. 9 shows the assessment of the derivative of the impedance waveform following an ECG-based detection for event confirmation. In this example, the graphs show the relative impedance and its derivative, for demonstrative purposes. Following detection of an R-wave at 230, it can be seen that the impedance derivative shows a significant peak, as shown at 232. However, following detection of a T-wave at 234, a much smaller peak in the impedance derivative is observed, as shown at 236.

The method is displayed in block form again. Following an ECG-based event detection at 240, the method checks the derivative of the impedance waveform during a time period following the ECG detection, as shown at 242. If there is a large peak observed, as shown at 244, then an R-wave is declared, as shown at 246. Otherwise the method flows through block 248 and a misdetection is declared, as noted at 250.

Figure 10:
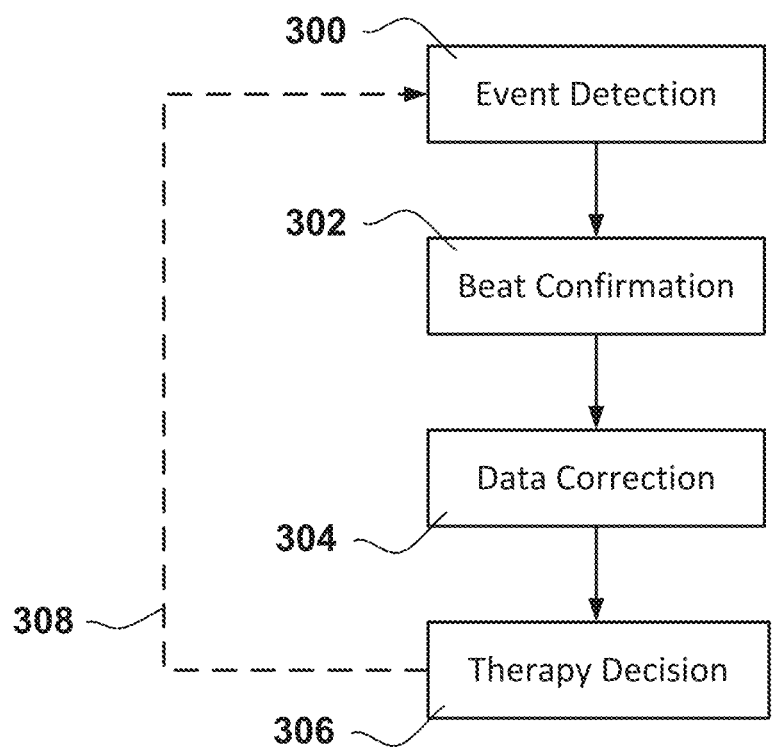
FIG. 10 is a block diagram showing an illustrative method of cardiac signal analysis.

FIG. 10 is a block diagram showing an illustrative method of cardiac signal analysis. In this illustrative example, an overall method of cardiac signal analysis for an implantable therapy system, such as an implantable defibrillator, is shown. The process shown is cyclical and begins with event detection, as shown at 300. Event detection can be based on comparing the amplitude of received ECG signal to a threshold, where the threshold typically (but not necessarily) varies with time, such as examples in U.S. Pat. No. 8,565,878 or 5,709,215, each of which is incorporated herein by reference.

Next, the method performs beat confirmation, as shown at 302. Beat confirmation 302 may include steps to identify noise, such as in US Pat. App. Pub. No. 2011-0098775 or U.S. Pat. No. 7,248,921, for example, each of which are incorporated herein by reference. Beat confirmation may also include steps to identify overdetection such as those in U.S. Pat. No. 8,160,686 or 8,160,687, each of which is incorporated herein by reference. The methods discussed above with reference to any of FIGS. 5-9 may also be part of the beat confirmation 302.

Next, as needed, data correction 304 is performed. Data correction can be used to address any beats that are not confirmed in beat confirmation 302. Depending on the level of certainty or doubt surrounding a given beat which cannot be confirmed, the beat and the intervals before and after it can be declared suspect and discarded or, instead, the only the beat is discarded, and the intervals that surround it are combined into a single longer interval for later use in rate calculation or other signal analysis. Again, U.S. Pat. Nos. 8,160,686 and 8,160,687 provide illustrative examples.

In alternative examples, rather than a data correction 304, a system that identifies misdetections in block 302 may take other steps including, for example, activating or switching to a different sensing configuration for the underlying system. For example, a different sensing vector can be chosen for use. An alarm may be set to suggest that the patient go to clinic, or a communication may be generated or placed in queue for transmission to a home monitoring system. In another example, if beat confirmation fails to confirm a threshold quantity of beats in a given time frame, a pending therapy, such as a defibrillation shock, may be delayed or inhibited.

The method continues with therapy decision, as shown at 306. Numerous methods are known in the art for therapy decisions, including examples discussed in detail in U.S. Pat. Nos. 7,330,757, 8,160,686, and 8,160,697. Some methods include the use of one or more "NID" counters, with NID meaning the number of intervals to detect. Multiple NID counters may be used, such as a first counter for ventricular tachyarrhythmia to trigger anti-tachycardia pacing, and a second counter for ventricular fibrillation to trigger defibrillation therapy delivery. Therapy decisions may also be made using factors calling for persistence, high rate conditions, poor match to morphology templates of normal rhythm, signal width, and other factors. Morphology analysis may include correlation waveform analysis (CWA), such as full, classic CWA or a simplified difference of area CWA, wavelet transforms, frequency transform, principal component analysis, probability distribution function, or other assessments.

Therapy decision 306 may include a call to initiate charging of a high voltage capacitor (or capacitor bank) for purposes of delivering high power defibrillation therapy. Therapy decision 306 may instead call for delivery of pacing therapy, whether bradycardia pacing for rates that are too low, or anti-tachycardia pacing for monomorphic ventricular tachyarrhythmia. Where therapy decision 306 calls for capacitor charging, there may be several seconds of charging needed before therapy will be available, and the method may iterate as shown at 308 while charging continues. Iteration 308 would also take place if no therapy is needed.

Figure 11:
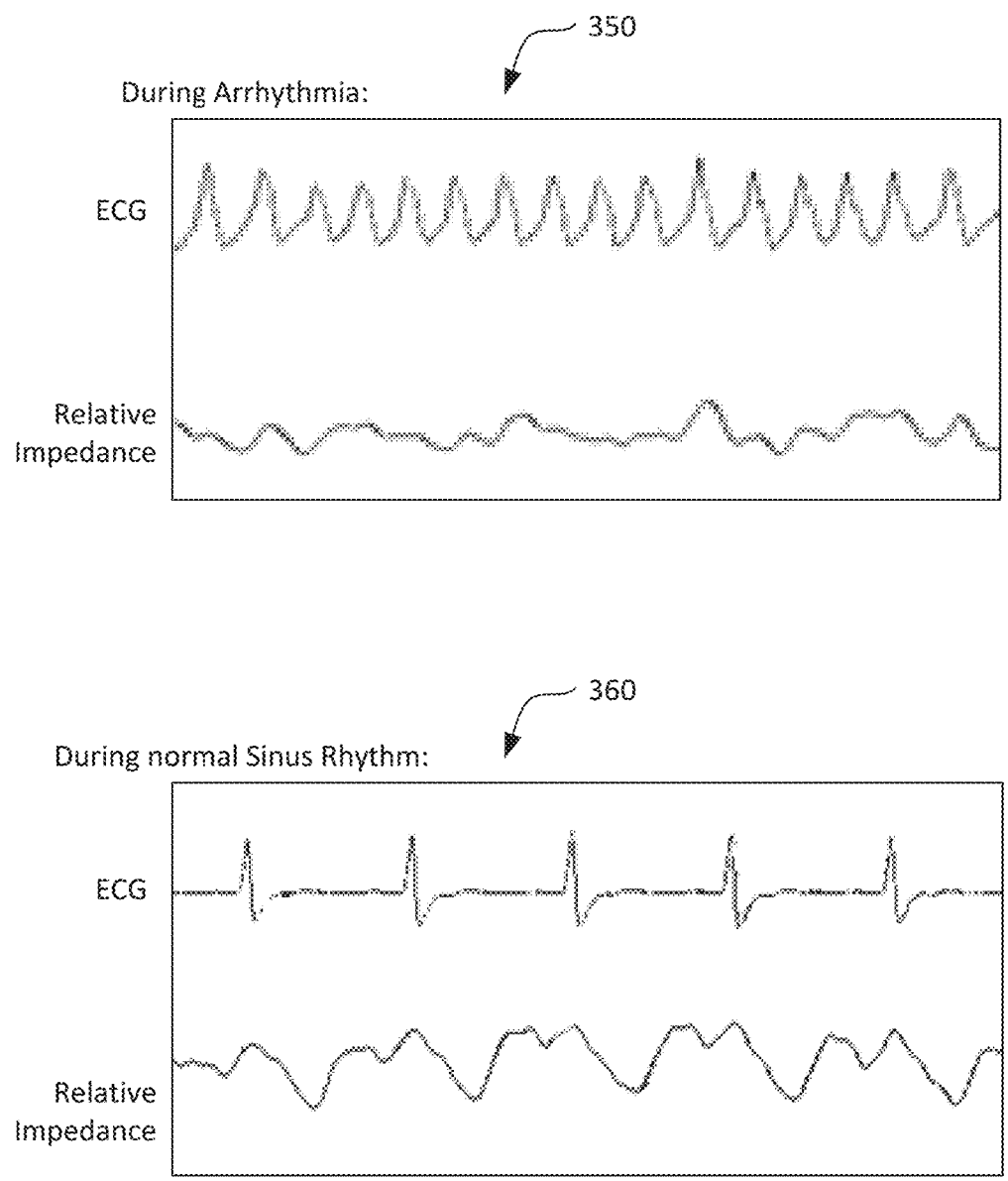
FIG. 11 compares the ECG and impedance waveform during an arrhythmia to that during a normal rhythm.

FIG. 11 provides a comparison between the impedance waveform captured during an arrhythmia versus that captured during a sinus rhythm. As shown at 350, during a tachyarrhythmia (which in the data shown was a ventricular fibrillation at approximately 280 bpm), the relative impedance waveform is general uncorrelated to the arrhythmia waveform. Meanwhile, during the normal sinus rhythm, the relative impedance tracks cycles along with the ECG, as shown at 360. Thus the impedance waveform may itself provide an arrhythmia identification tool. In addition, the impedance waveform is likely more useful for verification of detected events during the normal rhythm at 360 than it is during the arrhythmia at 350.

In another alternative embodiment, an impedance waveform template may be created. A static template may be formed by capturing the impedance waveform in a window associated with a detected beat and storing a "pre-template". The pre-template may be confirmed by comparison to one or more subsequently detected impedance waveforms captured in similar manner to the pre-template and, if the impedance waveforms captured after the pre-template match the pre-template, the pre-template can be confirmed and stored as a static template. Later detections can be confirmed by comparing the impedance waveform associated with such later detections with the static template. In another alternative, a dynamic impedance waveform template may be used by comparing one beat's impedance waveform to that of a preceding beat or an average of several preceding beats.

Figure 12:
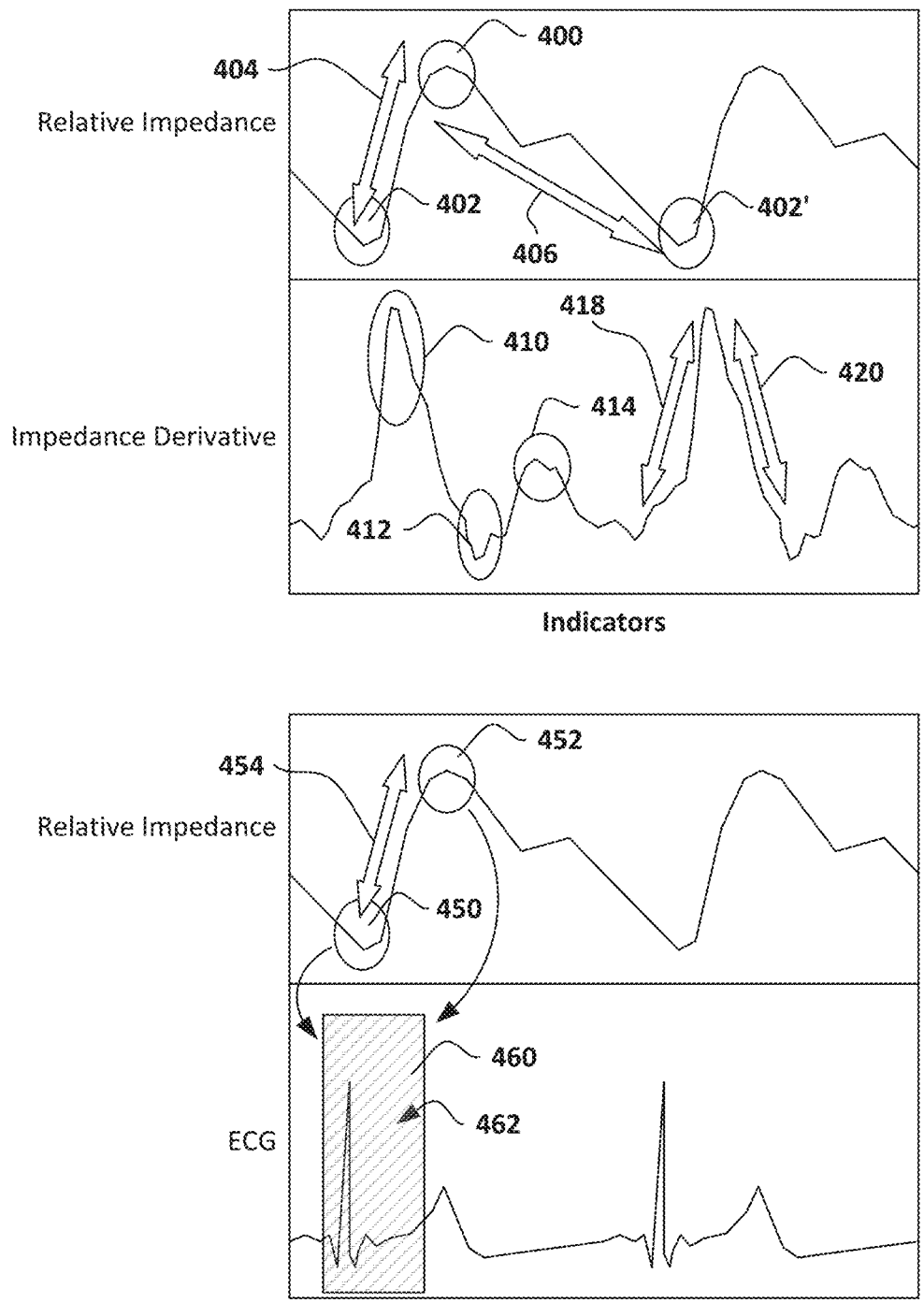
FIG. 12 illustrates an alternative embodiment in which characteristics of the impedance waveform are used to trigger R-wave detection.

FIG. 12 shows an alternative embodiment in which indicators from the impedance waveform are used to define a window for searching for an R-wave. In the upper portion of the Figure, various indicators are identified and numbered. These include the positive peak 400 and negative peak 402 of the relative impedance, the slope 404 following the negative peak 402 and preceding the positive peak 400, and the slope 406 between the positive peak 400 and a subsequent negative peak 402'. Slope 404 is steep and upward, while slope 406 is gradual and downward. In one example, the existence of a negative peak 402 and positive peak 400, with a sufficiently steep slope 404 therebetween gives an inference that an R-wave has occurred.

The impedance derivative includes various features including the positive peak 410 and negative peak 412, an intermediate peak 414 and slopes 418 and 420. The length of slopes 418 and 420, for example, may be used to identify a likely R-wave, allowing a window to be defined in the ECG for searching for an R-wave. In another example, consecutive positive, high peaks 410 with an intermediate lower peak 414 can be used to infer that there should be R-waves corresponding to the two positive peaks 410. Then R-wave search windows may be defined.

In a specific example, a negative peak 450 and positive peak 452 are identified, and the path length of the slope 454 therebetween may be assessed for its characteristics—that is, the path should not have a turning point, such that the path length 454 would equal the difference in amplitude between peaks 450 and 452. This contrasts with a slope that includes a T-wave, such as slope 406, above. Having identified qualifying features 450, 452, 454, in the relative impedance, the system sets a search window 460 for use in the ECG, in order to identify an R-wave peak 462. In this example, the search window 460 is set to approximately the time period between peaks 450 and 452, but is offset to be earlier in time by 20-100 milliseconds, for example. The actual duration of window 460 may be variable or preset, as desired, with illustrative settings of 50-200 milliseconds, for example. Other values may be used instead.

Additional or different features may be used. For example, a negative peak, followed by a positive peak, with no inflection points or few (<2) inflection points therebetween may be used to trigger a search window, as this would correspond to the relative impedance waveform associated with the R-wave. The time between the peaks may be checked as well, to ensure that the correct interval is being searched. For example, the interval between negative peak 402 and positive peak 400 is quite a bit shorter than the interval between positive peak 400 and the subsequent negative peak 402'. Checking this interval, as well as the slope direction, can assist in correctly setting the search window 460.

Referring briefly back to FIG. 1, certain physical details of an implemented system are noted. The canister 12 preferably contains operational circuitry for the implantable system. The operational circuitry may include a controller and any suitable analog and/or digital circuits needed for signal processing, memory storage and generation of high-power electrical, low-power electrical and/or non-electrical outputs. The operational circuitry may be coupled to suitable battery technology for an implantable device, with any of numerous examples well known in the art (often incorporating Lithium in one form or another), and may use various capacitor technologies to assist in the short term build-up and/or storage of energy for defibrillation or other high output purposes.

The lead 14 and external shell for the canister 12 can be manufactured with various materials suitable for implantation, such as those widely known, along with coatings for such materials, throughout the art. For example, the canister 12 can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. Other materials, such as stainless steel may instead be used, with various sputtered or otherwise applied coatings, as needed or desired, on the canister 12. The electrodes 16, 18, and 20 can be formed of suitable materials as well, such as silver, gold, titanium or stainless steel such as MP35N stainless steel alloy, or other materials. Various suture sleeves and other anchoring elements may be provided and/or used as well.

Various alternatives and details for these designs, materials and implantation approaches are known to those skilled in the art. Commercially available systems having hardware for performing the sensing and signal analysis shown above may include the Boston Scientific Teligen® ICD and S-ICD® System, Medtronic Concerto® and Virtuoso® systems, and St. Jude Medical Promote® RF and Current® RF systems. Additional circuitry or configuration effort may be needed in any of these systems to allow the monitoring of impedance as discussed. For example, in heart failure devices, impedance monitoring can be used for fluid assessment purposes, with advancing heart failure detected by monitoring chest fluid levels, which are manifested by lower transthoracic impedance as poorly conducting air is displaced by accumulating and more conductive fluids.

FIG. 1 illustrates a subcutaneous-only placement. However, the sensing methods discussed above may be implemented in various ways on a transvenous system. In one example, an additional subcutaneous lead is provided on a transvenous system, with placement parallel to the aorta to enable an impedance sensing circuit to provide impedance waveform data useful for beat confirmation.

The impedance waveform analysis discussed above may be used in implantable defibrillators and in other medical devices. Some examples include implantable pacemakers, implantable cardiac (or other) monitoring devices, drug delivery devices, neurostimulators, and neuromodulators. In some examples there may be multiple implanted devices which communicate with one another, in which one system provides data relating to the impedance waveform or analysis thereof to the other system via conducted or wireless communication, for example. An implantable system may communicate with an external system as well, for example, with either system providing data related to the impedance waveform to the other.

The methods demonstrated above may be used independent of one another, or may be used in various combinations. For example, the integral of relative impedance may be used in combination with the relative impedance peak alignment to characterize detected events. In another example, the integral of relative impedance may be used in combination with the relative or differentiated slope after the R-wave detection. In yet another example, the integral of relative impedance is used with the differentiated relative impedance peak following R-wave detection. In an example, the relative impedance peak alignment is reviewed in combination with the relative or differentiated slope following detection. In another example, the relative impedance peak alignment to a detection is reviewed in combination with the differentiated relative impedance peak following a detection. In yet another example, the relative or differentiated slope following a detection is reviewed in combination with a determination of whether the differentiated relative impedance demonstrates a post-detection peak. The results of these paired combinations may apply cooperatively, in which both rules must be met to declare misdetection or disjointly, in which meeting either rule will declare misdetection.

In a further example, the assessment outcome for one or more of elements 114, 116, 118 and 120 in FIG. 5 may be subject to ambiguity. For example, the integral of relative impedance between two detections may be reviewed and compared to first and second thresholds in which, if the first threshold is met, then accurate detection is confirmed, if the second threshold is met, misdetection is declared, and if the result falls between the first and second thresholds, ambiguity is found. When ambiguity is found, in one example, a second or further tier of analysis is called to use. For example, if the outcome of analysis under 114 is ambiguous, then the assessment of 116, 118 or 120 may be called in addition to 114.

VARIOUS NOTES & EXAMPLES

A first example takes the form of an implantable cardiac stimulus device comprising operational circuitry for monitoring and analyzing cardiac signals and a plurality of electrodes including at least two electrodes configured for current injection and at least two electrodes configured for electrical monitoring of voltage resultant from the injected current to allow the operational circuitry to generate an impedance waveform for monitoring purposes, the operational circuitry configured to perform the following: inject current and sense resultant voltage to generate an impedance waveform; capture an electrocardiogram (ECG) signal using the electrodes; detect an event in the ECG; analyze a portion of the impedance waveform relative to the detected event; and determine whether the detected event is an overdetection using the analysis of the impedance waveform.

In a further illustration of the first example, the operational circuitry is configured to analyze a portion of the impedance waveform relative to the detected event by: calculating an integral of the impedance waveform between the detected event and an adjacent-in-time detected event; comparing the integral to an expected value; and if integral does not match the expected value, determining that one of the detected event or the adjacent-in-time detected event is an overdetection; or if the integral matches the expected value, determining that a complete cardiac cycle has occurred between the detected event and the adjacent in time detected event.

In another further illustration of the first example, the expected value is calculated using an average impedance and a length of an interval between the detected event and the adjacent in time detected event. In yet another further illustration of the first example, the operational circuitry is configured to analyze a portion of the impedance waveform relative to the detected event by: defining a window within the impedance waveform to correlate, in time, with a peak in the ECG signal associated with the detected event; determine whether a positive peak appears in the impedance waveform in the defined window; and if there is a positive peak in the impedance waveform in the defined window, determining that the detected event is an overdetection.

In another further illustration of the first example, the operational circuitry is configured to analyze a portion of the impedance waveform relative to the detected event by: defining a window within the impedance waveform to correlate, in time, with a peak in the ECG signal associated with the detected event; determining whether a negative peak appears in the impedance waveform in the defined window; and if there is no negative peak in the impedance waveform in the defined window, determining that the detected event is an overdetection.

In another further illustration of the first example the operational circuitry is configured to analyze a portion of the impedance waveform relative to the detected event by: defining a window within the impedance waveform at a time after a peak in the ECG signal associated with the detected event; determining whether there is an upward slope in the impedance waveform during the defined window; and if there is an upward slope, determining that the detected event is not an overdetection.

In another further illustration of the first example the operational circuitry is configured to analyze a portion of the impedance waveform relative to the detected event by: defining a window within the impedance waveform at a time after a peak in the ECG signal associated with the detected event; determining whether there is a downward slope in the impedance waveform during the defined window; and if there is a downward slope, determining that the detected event is an overdetection.

In another further illustration of the first example the operational circuitry is configured to analyze a portion of the impedance waveform relative to the detected event by: calculating a derivative of the impedance waveform; defining a window within the derivative of the impedance waveform at a time after a peak in the ECG signal associated with the detected event; and determining whether a peak meeting threshold criteria appears in the defined window of the derivative of the impedance waveform.

In another further illustration of the first example the operational circuitry is configured to analyze a portion of the impedance waveform relative to the detected event by: defining a window within the impedance waveform at a time after a peak in the ECG signal associated with the detected event; and comparing the impedance waveform to a stored template of the impedance waveform.

In another further illustration of the first example the operational circuitry is further configured to calculate a cardiac rate using only detected events that are not overdetections.

A second example takes the form of a method of operation in an implantable cardiac stimulus device having operational circuitry for monitoring and analyzing cardiac signals and a plurality of electrodes including at least two electrodes configured for current injection and at least two electrodes configured for electrical monitoring of voltage resultant from the injected current to allow the operational circuitry to generate an impedance waveform for monitoring purposes, the method comprising: the operational circuitry injecting current and sensing resultant voltage to generate an impedance waveform; the operational circuitry capturing an electrocardiogram (ECG) signal using the electrodes; the operational circuitry detecting an event in the ECG; the operational circuitry analyzing a portion of the impedance waveform relative to the detected event; and the operational circuitry determining whether the detected event is an overdetection using the analysis of the impedance waveform.

In a further illustration of the second example the step of analyzing a portion of the impedance waveform relative to the detected event is performed by the operational circuitry doing the following: calculating an integral of the impedance waveform between the detected event and an adjacent-in-time detected event; comparing the integral to an expected value; and if integral does not match the expected value, determining that one of the detected event or the adjacent-in-time detected event is an overdetection; or if the integral matches the expected value, determining that a complete cardiac cycle has occurred between the detected event and the adjacent in time detected event.

In another further illustration of the second example the step of analyzing a portion of the impedance waveform relative to the detected event is performed by the operational circuitry doing the following: defining a window within the impedance waveform to correlate, in time, with a peak in the ECG signal associated with the detected event; determine whether a positive peak appears in the impedance waveform in the defined window; and if there is a positive peak in the impedance waveform in the defined window, determining that the detected event is an overdetection.

In another further illustration of the second example the step of analyzing a portion of the impedance waveform relative to the detected event is performed by the operational circuitry doing the following: defining a window within the impedance waveform to correlate, in time, with a peak in the ECG signal associated with the detected event; determining whether a negative peak appears in the impedance waveform in the defined window; and if there is no negative peak in the impedance waveform in the defined window, determining that the detected event is an overdetection.

In another further illustration of the second example the step of analyzing a portion of the impedance waveform relative to the detected event is performed by the operational circuitry doing the following: defining a window within the impedance waveform at a time after a peak in the ECG signal associated with the detected event; determining whether there is an upward slope in the impedance waveform during the defined window; and if there is an upward slope, determining that the detected event is not an overdetection.

In another further illustration of the second example the step of analyzing a portion of the impedance waveform relative to the detected event is performed by the operational circuitry doing the following: defining a window within the impedance waveform at a time after a peak in the ECG signal associated with the detected event; determining whether there is a downward slope in the impedance waveform during the defined window; and if there is a downward slope, determining that the detected event is an overdetection.

In another further illustration of the second example the step of analyzing a portion of the impedance waveform relative to the detected event is performed by the operational circuitry doing the following: calculating a derivative of the impedance waveform; defining a window within the derivative of the impedance waveform at a time after a peak in the ECG signal associated with the detected event; and determining whether a peak meeting threshold criteria appears in the defined window of the derivative of the impedance waveform.

In another further illustration of the second example the step of analyzing a portion of the impedance waveform relative to the detected event is performed by the operational circuitry doing the following: defining a window within the impedance waveform at a time after a peak in the ECG signal associated with the detected event; and comparing the impedance waveform to a stored template of the impedance waveform.

In another further illustration of the second example the operational circuitry is further configured to calculate a cardiac rate using only detected events that are not overdetections.

A third example takes the form of a method of operation in an implantable cardiac stimulus device having operational circuitry for monitoring and analyzing cardiac signals and a plurality of electrodes including at least two electrodes configured for current injection and at least two electrodes configured for electrical monitoring of voltage resultant from the injected current to allow the operational circuitry to generate an impedance waveform for monitoring purposes, the method comprising: the operational circuitry injecting current and sensing resultant voltage to generate an impedance waveform; the operational circuitry capturing an electrocardiogram (ECG) signal using the electrodes; the operational circuitry identifying one or more indicators of a likely cardiac event in the impedance waveform; the operational circuitry defining an interval in the ECG; and the operational circuitry identifying a cardiac event in the ECG interval.

A fourth example takes the form of a method of generating an impedance waveform using an implantable cardiac system, the implantable cardiac system including a canister and at least one lead attached thereto with a plurality of electrodes, with the canister containing operational circuitry for the implantable cardiac system, the method comprising: generating a plurality of samples of impedance by: injecting a current using the canister, with the canister implanted near the left axilla and approximately level with the apex of the heart, and an electrode on the lead, the electrode on the lead being implanted adjacent the sternum; and observing a resultant voltage from the injected current; and combining the plurality of samples into a waveform; in which the injected current is in the range of 1 microamp to 4 milliamps in amplitude with an applied frequency in the range of 1 kHz to 1 MHz, and in which the samples are taken at a sampling rate in the range of 128 Hz to 1024 Hz.

In a further illustration of the fourth example, the plurality of samples are captured generally continuously during the occurrence of a prespecified condition.

In another further illustration of the fourth example, the implantable cardiac system capturing an ECG signal and analyzing the ECG signal to detect events in the ECG signal, wherein the plurality of samples are captured in response to the implantable cardiac system detecting an event in the ECG signal for a period of at least 100 ms.

A fifth example takes the form of an implantable cardiac system, the implantable cardiac system including a canister and at least one lead attached thereto with a plurality of electrodes, the canister housing operational circuitry that is coupled to the plurality of electrodes to receive electrical signals therefrom and provide electrical outputs thereto, the operational circuitry configured to perform a method of generating an impedance waveform comprising: generating a plurality of samples of impedance by: injecting a current using the canister, with the canister implanted near the left axilla and approximately level with the apex of the heart, and an electrode on the lead, the electrode on the lead being implanted adjacent the sternum; and observing a resultant voltage from the injected current; and combining the plurality of samples into a waveform; in which the injected current is in the range of 1 microamp to 4 milliamps in amplitude with an applied frequency in the range of 1 kHz to 1 MHz, and in which the samples are taken at a sampling rate in the range of 32 Hz to 1024 Hz.

In a further illustration of the fifth example, the operational circuitry is configured to capture the plurality of samples generally continuously during the occurrence of a prespecified condition.

In another further illustration of the fifth example, the operational circuitry is further configured to capture an ECG signal and analyze the ECG signal to detect events in the ECG signal; and the operational circuitry is configured such that the plurality of samples are captured in response an event being detected in the ECG signal, for a period of at least 100 MS.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of operation in an implantable cardiac stimulus device having operational circuitry for monitoring and analyzing cardiac signals and a plurality of electrodes including at least two electrodes configured for current injection and at least two electrodes configured for electrical monitoring of voltage resultant from the injected current to allow the operational circuitry to generate an impedance waveform for monitoring purposes, the method comprising:
    the operational circuitry injecting current using the at least two electrodes configured for current injection and sensing resultant voltage using the at least two electrodes configured for electrical monitoring to generate an impedance waveform;
    the operational circuitry capturing an electrocardiogram (ECG) signal using a combination of the plurality of electrodes selected for sensing an ECG signal;
    the operational circuitry detecting an event in the ECG;
    the operational circuitry analyzing a portion of the impedance waveform relative to the detected event; and
    the operational circuitry determining whether the detected event is an overdetection using the analysis of the impedance waveform.

2. The method of claim 1 wherein the step of analyzing a portion of the impedance waveform relative to the detected event is performed by the operational circuitry doing the following:
    calculating an integral of the impedance waveform between the detected event and an adjacent-in-time detected event;
    comparing the integral to an expected value; and
    if the integral does not match the expected value, determining that one of the detected event or the adjacent-in-time detected event is an overdetection; or
    if the integral matches the expected value, determining that a complete cardiac cycle has occurred between the detected event and the adjacent in time detected event.

3. The method of claim 1 wherein the step of analyzing a portion of the impedance waveform relative to the detected event is performed by the operational circuitry doing the following:
    defining a window within the impedance waveform to correlate, in time, with a peak in the ECG signal associated with the detected event;
    determine whether a positive peak appears in the impedance waveform in the defined window; and
    in response to determining there is the positive peak in the impedance waveform in the defined window, determining that the detected event is an overdetection.

4. The method of claim 1 wherein the step of analyzing a portion of the impedance waveform relative to the detected event is performed by the operational circuitry doing the following:
    defining a window within the impedance waveform to correlate, in time, with a peak in the ECG signal associated with the detected event;
    determining whether a negative peak appears in the impedance waveform in the defined window; and
    in response to determining there is no negative peak in the impedance waveform in the defined window, determining that the detected event is an overdetection.

5. The method of claim 1 wherein the step of analyzing a portion of the impedance waveform relative to the detected event is performed by the operational circuitry doing the following:
    defining a window within the impedance waveform at a time after a peak in the ECG signal associated with the detected event;
    determining whether there is an upward slope in the impedance waveform during the defined window; and
    in response to determining there is the upward slope, determining that the detected event is not an overdetection.

6. The method of claim 1 wherein the step of analyzing a portion of the impedance waveform relative to the detected event is performed by the operational circuitry doing the following:
    defining a window within the impedance waveform at a time after a peak in the ECG signal associated with the detected event;
    determining whether there is a downward slope in the impedance waveform during the defined window; and
    in response to determining there is the downward slope, determining that the detected event is an overdetection.

7. The method of claim 1 wherein the step of analyzing a portion of the impedance waveform relative to the detected event is performed by the operational circuitry doing the following:
    calculating a derivative of the impedance waveform;
    defining a window within the derivative of the impedance waveform at a time after a peak in the ECG signal associated with the detected event; and
    determining whether a peak meeting threshold criteria appears in the defined window of the derivative of the impedance waveform.

8. The method of claim 1 wherein the step of analyzing a portion of the impedance waveform relative to the detected event is performed by the operational circuitry doing the following:

defining a window within the impedance waveform at a time after a peak in the ECG signal associated with the detected event; and comparing the impedance waveform to a stored template of the impedance waveform.

9. The method of claim 1 wherein the operational circuitry is further configured to calculate a cardiac rate using only detected events that are not overdetections.

10. An implantable cardiac stimulus device comprising:
a canister having an external shell composed of material suitable for implantation;
a plurality of electrodes exposed external to the external shell of the canister including electrodes configured to inject current and electrodes configured to monitor a resultant voltage from the injected current;
operational circuitry, disposed within the canister, operatively coupled to the plurality of electrodes, the operational circuitry including:
sensing circuitry configured to sense the resultant voltage and capture an electrocardiogram (ECG) signal; and
a controller configured to:
generate an impedance waveform from the resultant voltage;
detect an event in the ECG;
analyze a portion of the impedance waveform relative to the detected event; and
determine whether the detected event is an overdetection using the analysis of the impedance waveform; and
a power source disposed within the canister and configured to power the operational circuitry.

11. The device of claim 10 wherein analyzing a portion of the impedance waveform relative to the detected event is performed by the controller being further configured to:
calculate an integral of the impedance waveform between the detected event and an adjacent-in-time detected event;
compare the integral to an expected value; and
if the integral does not match the expected value, determine that one of the detected event or the adjacent-in-time detected event is an overdetection; or
if the integral matches the expected value, determine that a complete cardiac cycle has occurred between the detected event and the adjacent in time detected event.

12. The device of claim 10 wherein analyzing a portion of the impedance waveform relative to the detected event is performed by the controller being further configured to:
define a window within the impedance waveform to correlate, in time, with a peak in the ECG signal associated with the detected event;
determine whether a positive peak appears in the impedance waveform in the defined window; and
in response to determining the positive peak appears in the impedance waveform in the defined window, determine that the detected event is an overdetection.

13. The device of claim 10 wherein analyzing a portion of the impedance waveform relative to the detected event is performed by the controller being further configured to:
define a window within the impedance waveform to correlate, in time, with a peak in the ECG signal associated with the detected event;
determine whether a negative peak appears in the impedance waveform in the defined window; and
in response to determining the negative peak does not appear in the impedance waveform in the defined window, determine that the detected event is an overdetection.

14. The device of claim 10 wherein analyzing a portion of the impedance waveform relative to the detected event is performed by the controller being further configured to:
define a window within the impedance waveform at a time after a peak in the ECG signal associated with the detected event;
determine whether there is an upward slope in the impedance waveform during the defined window; and
in response to determining there is the upward slope, determine that the detected event is not an overdetection.

15. The device of claim 10 wherein analyzing a portion of the impedance waveform relative to the detected event is performed by the controller being further configured to:
define a window within the impedance waveform at a time after a peak in the ECG signal associated with the detected event;
determine whether there is a downward slope in the impedance waveform during the defined window; and
in response to determining there is the downward slope, determine that the detected event is an overdetection.

16. The device of claim 10 wherein analyzing a portion of the impedance waveform relative to the detected event is performed by the controller being further configured to:
calculate a derivative of the impedance waveform;
define a window within the derivative of the impedance waveform at a time after a peak in the ECG signal associated with the detected event; and
determine whether a peak meeting threshold criteria appears in the defined window of the derivative of the impedance waveform.

17. The device of claim 10 wherein analyzing a portion of the impedance waveform relative to the detected event is performed by the controller being further configured to:
define a window within the impedance waveform at a time after a peak in the ECG signal associated with the detected event; and
compare the impedance waveform to a stored template of the impedance waveform.

18. The device of claim 10 wherein the controller is further configured to calculate a cardiac rate using only detected events that are not overdetections.

* * * * *